United States Patent [19]

Lukácsovich et al.

[11] Patent Number: 5,160,489
[45] Date of Patent: Nov. 3, 1992

[54] EXPRESSION VECTORS AND METHOD FOR THEIR CONSTRUCTION

[75] Inventors: Tamás Lukácsovich; Pal Venetianer, both of Szeged; Tamàs Gaàl, Budapest; Imre Boros; Gabriella Balikó, both of Szeged, all of Hungary

[73] Assignee: Richter Gedeon Vegyeszeti Gyar R.T., Budapest, Hungary

[21] Appl. No.: 466,259
[22] PCT Filed: Sep. 14, 1988
[86] PCT No.: PCT/HU88/00061
§ 371 Date: Mar. 16, 1990
§ 102(e) Date: Mar. 16, 1990
[87] PCT Pub. No.: WO89/02466
PCT Pub. Date: Mar. 23, 1989

[30] Foreign Application Priority Data

Sep. 16, 1987 [HU] Hungary ............... 4111/87

[51] Int. Cl.⁵ ............ C12N 15/00; C12P 21/06
[52] U.S. Cl. .................. 435/172.3; 935/6; 935/10; 935/22; 935/41; 435/69.1
[58] Field of Search .......... 435/172.3, 69.1; 935/6, 935/10, 22, 41

[56] References Cited

U.S. PATENT DOCUMENTS 4,551,433 11/1985 De Boer .................. 435/253

OTHER PUBLICATIONS

Brosius et al., PNAS 81: 6929. 1984.
Thayer et al., Mol. Gen. Genet 199: 55. 1985.
Luckcsovich et al., J. of Bact. 169(1): 272. 1987.

Primary Examiner—Elizabeth C. Weimer
Assistant Examiner—Suzanne Ziska
Attorney, Agent, or Firm—Herbert Dubno; Jonathan Myers

[57] ABSTRACT

The invention relates to new expression vectors. More particularly, the invention relates to expression vectors carrying a new type of promoters for the expression of the foreign gene, which was constructed from promoter $P_2$ of E. coli ribosomal RNA operon and some regulatory sequences of E. coli las operon. The invention further relates to a method for the construction of the above vectors. The method is characterized by deleting most part of the structurgenes of E. coli ribosomal RNA operon (rrn operon) built in a suitable vector, joining together the part of operon rrn comprising promoter $P_2$ with the beginning part of the lac operon outside the regions $-35$ and $-10$, downstream of them so as to create a new NsiI cleavage site at the joining point of the sequences originating from rrn and lac operons, deleting the inner TGCA sequence-element of the newly created NsiI cleavage site and building the structurgene to be expressed between these newly created regulatory sequences.

11 Claims, 7 Drawing Sheets

Nucleotide sequence of the joining regions of the parts of different origin in plasmid pER-VI/23

Joining region of the beginning part of the gene for the 16SrRNA molecule and the end-part of the gene for the 23S rRNA molecule in plasmid pBB9Δ9:

GTAGGTGGGGTAACGGCTCATGAACCGTGAGGCCTTAACCTT
Nucleotide 260 of the mature 16S rRNA    last nucleotide of the mature 23S rRNA
    molecule    molecule Joining region of the part of bacterial origin and the part of pBr 322 origin in plasmid pBB9b28

ATCCCTGGCAGTATGCAACCCTGCCTGCGCGCTTTCGGTGA
DNA of bacterial origin downstream    nucleotide 2080 of pBR 322
of the rrnB operon Joining region of pBR 322 and the promoter region of operon rrnB in plasmid p419-10

CACATTTCCCGAAAAGTGCCCACTGACACGGAACAACGG
nucleotide 4260 of pBR 322    promoter region of rrnB

FIG.3 a./ pER VI/23

```
AGAGAAAGCAAAAATAAATGCTTGACTCTGTAGCGGGAAGGCCGTATTATGCATGG
. . . . . . . . . . . . . .    ─────────────            ══════════
                                -35 region                -10 region
```

```
                                                        AluI
AATTGTGAGCGGATAACAATTTCACACAGGAAACAGCTATGACC
xx                           ─ ─ ─ ─ ─ ─~~~~~~~~─ ─ ─ ─ ─
───lac operator───                                   MetThr
                                                   half PvuII
``` b./ pER VI/23 [-Nsi]

```
AGAGAAAGCAAAAATAAATGCTTGACTCTGTAGCGGGAAGGCCGTATTATGG
. . . . . . . . . . . . . .    ─────────────            ══════════
                                -35 region                -10 region
```

```
AATTGTGAGCGGATAACAATTTCACACAGGAAACAGCTATGACC
xx                           ─ ─ ─ ─ ─ ─~~~~~~~~─ ─ ─ ─ ─ ─
───lac operator───                                   MetThr
```

FIG.7

Nucleotide sequence of the Hind III Hind III polylinker of πVX origin in the orientation as present in plasmid PLH4

5'
HindIII                               EcoRI           BamHI
  ClaI
AAGCTTATCGATGATAAGCTGTCAAACATGAGAATTCGCGCGACCGGATC
       10        20        30        50        50

PstI
CGGGCAACGTTGTTCCCATTGCTGCAGGCGGAGAACTGGTAGGTATGGAA
       60        70        80        90        100

BgIII    HindIII
   XbaI
GATCTCTAGAAGCTT

EXPRESSION VECTORS AND METHOD FOR THEIR CONSTRUCTION

FIELD OF THE INVENTION

The invention relates to new expression vectors carrying a novel type of promoters which are constructed of the $P_2$ promoter of a ribosomal RNA operon (rrn B operon) of Escherichia coli and some regulatory sequences from the lac operon of E. coli. The invention further relates to a method for constructing the above mentioned novel promoters and new expression vectors.

BACKGROUND OF THE INVENTION

Genes of any origin carrying any type of information can be introduced into bacterial cells by means of in vitro DNA recombination, as it is widely known. Stable maintenance of the foreign DNA and the expression of the information for which it codes can be carried out by means of appropriate carrier molecules, the expression vectors. When expressing a gene coding for a protein in bacterial cells, the enzymes of the bacterium firstly synthesize an mRNA copy on the DNA template during the course of transcription and a polypeptide chain afterwards, using the information coded in the RNA message, during the course of translation. Transcription is initiated at a DNA region called a promoter. RNA polymerase recognizes this DNA region and binds to it before the initiation of transcription. In vitro DNA recombination methods can be used economically in practice for the production of proteins only if these proteins are produced in relatively high amounts, that is both transcription and translation are effective. Therefore it is very important for promoters to be "strong" (besides other needed features), that is a suitably high level of transcription must be initiated on them.

Different expression vectors have been constructed by the use of many kinds of promoters, e.g. lac, trp, bla, llp, lambda $p_L$ promoters. The promoter of the lac operon has been widely used in practice mainly becouse of its well controlled functioning though it is a relatively week promoter. So called hybrid promoters of different origin have been described e.g. in European Patent Application No. 82302532.5 (publication number 0 06—540). These promoters are characterized by the fact that the so called −35 and −10 regions (which are) the most important regions of a well functioning promoter) are of different origin, that is the two promoter parts of different origin are joined together in the region between the −35 and −10 regions. According to the abovementioned patent application, expression vectors constructed with the use of such hybrid promoters are excellent for industrial purposes. Since their functioning is well controlled and they make efficient transcription possible at the same time.

OBJECT OF THE INVENTION

The object is to develop expression vectors carrying stronger promoters-to render good protein yields- which are at the same time well controlled.

SUMMARY OF THE INVENTION

At the beginning of our research project we carried out experiments using the expression vectors described in: Lukacsovich et al: New regulatory features of the promoters of an Escherichia coli rRNA gene (J. Bact. 169, 272–277) January 1987. The best functioning of these vectors carried promoters with the main features as follows:

they are constructed of a part coming from the $P_2$ promoter of a ribosomal operon (rrnB) of E. coli and a part coming from the regulatory sequences of the lac operon of E. coli, the two parts coming from the rrnB and lac operons are joined together downstream of the −10 region, both the −35 and −10 regions originate from the rrnB operon, while the GC rich region downstream of the −10 region in rrnB $P_2$ has been replaced by analogous sequences originating from the lac operon which do not show repressory effect, so it does not affect the strong functioning of the other parts of the promoter.

Though these promoters have been constructed by the combination of different parts of two different promoters, they can not be called hybrid promoters since the most important parts for functioning both the −35 and −10 regions originate from the same promoter, rrnB $P_2$. We found these promoters to render very good expression. Carrying out more experiments, we surprisingly found that after eliminating the four base pairs: TGCA downstream of the −10 region in vectors carrying the above characterized promoters, the intensity of the transcription doubles.

This finding is surprising for more than one reason. On the one hand there are not any hints in the art that the abovementioned four base pairs play any role in determining the strength of the promoter; on the other hand, doubling the intensity of the transcription is a very significant result in the case of promoters which are originally very strong.

On the basis of what was said above the present invention relates to promoters which are constructed of the $P_2$ promoter of a ribosomal operon (rrnB) of E. coli and of some regulatory sequences from the lac operon of E. coli wherein the two parts of said different origin are joined together downstream of the −10 region of the promoter and the TGCA sequence is deleted immediately downstream of the −10 region.

The present invention further relates to all expression vectors comprising the above mentioned promoters; E. Coli host cells transformed by these vectors and methods for constructing the said promoters and expression vectors.

The main features of the expression vectors of the present invention and the main characteristics of the gene-expression made possible by them, can be concluded as follows:

1. The novel type promoter (named: 6/23 [-Nsi]) which is the main characteristic of the above mentioned expression vectors, initiates very high, constant transcription rates independently of the physiological state of the host cell, which means more than 90% of the total de novo RNA synthesis of the host cell, and accordingly, an accumulation of the foreign gene-product as much as 30–80% of the total amount of cellular proteins occurs.

2. Termination of the transcription occurs at the double terminatory region originating from the rrnB operon.

3. The product of the transcription is a hybrid mRNA molecule which also contains an rRNA segment—originating from the rrnB operon—besides the foreign coding region, the stability of the message is higher this way and the half-life of this mRNA molecule is longer than the awerage mRNA half-lifetime.

4. Intensity of the transcription can be controlled through the built in lac operatory region.

5. Using several members of the said new vector-family, the foreign gene-product is synthesized as a fusion-protein. This, on the one hand, makes the gene-product more stable and, on the other hand, the presence of the gene-product can be detected and the level of gene-expression can be measured easily with the help of the fusion partner (alpha-peptide of beta-galactosicase). The foreign gene can also be built in these vectors downstream of lacZ' in a non-fusion form. This type of construction functions like a bacterial operon and the foreign gene-product is synthesized as an individual protein. In this type of construction, the foreign gene must also comprise an E. coli ribosome binding-site. In other members of this vector-family, the foreign gene can be built in with its beginning being the translation-start position with optimal spacing to the built in ribosome binding-site. In this type of construction, the ATG codon of the foreign gene ensures the correct initiation of the translation. If the foreign gene to be built in fails to have an ATG codon at the beginning, it can be helped with the attachment of a synthetic ClaI linker having an ATG sequence-element in it. Foreign genes having their own ribosome binding-sites can also be built into these vectors using other restriction endonuclease recognition sites.

6. We have deleted the downstream regulatory region of the ribosomal promoter when constructing the novel type promoters functioning in the vectors of the invention. Thus the characteristic control of ribosomal promoter function, which is very sensitive to the physiological conditions, was eliminated and the promoter functions at the highest rate possible independently of the physiological conditions.

7. Transcription is initiated at a cytosine base in the original ribosomal operon. Changing this base for adenine or guanine significantly increases the transcription activity of the promoter.

8. We have joined the regulatory regions of the lac operon to the said promoters. This arrangement does not affect the maximum transcription intensity under induced conditions while it makes possible to control the promoter-function similarly to that of the lac operon; and it prevents the constant very high level transcription and translation which would affect disadvantageously the metabolism of the host cell. 9. The preferred expression vectors of the present invention are further characterized by having a size of 2800-4500 basepairs; carrying a gene providing resistance to ampicillin; an optimized spacing between the transcription and translation signals; a known total DNA sequence; a replication type Col El; a copy-number of 20-30 per cell (but we have also constructed the high copy-number version of several members of the said vector-family, according to the method of Hungarian Patent Application published under the number T/35280); several different restriction endonuclease recognition sites for building in the foreign gene to be expressed where the foreign gene can be built in at all three reading frames.

The new expression vectors described in the following examples contain the following restriction endonuclease recognition sites: e.g. PvuII, HindIII, ClaI, EcoRI. BamHI, BglII, XbaI, HpaI.

The method of the present invention for constructing the said expression vectors advantageously comprises the following steps (later to be described in detail):

1. Cloning the rrnB operon of E. coli in to the vector pBR322.

2. Stable subcloning the promoters of the said operon into plasmids, deleting the main part of the structural gene; placing the transcription start (promoter) and stop (terminator) regions close to each other.

3. Joining the beginning part of the lac operon to the shortened rrnB operon.

4. Constructing promoter 6/23 with the suitable control regions. Modifying this promoter to get the promoter 6/23[-Nsi].

5. Introducing different restriction sites into a suitable part of the vector making possible to build the foreign gene in. Developing different individual expression vector constructions.

Further details of the present invention will be illustrated in the following examples without restricting of our claim to the described vectors.

Example 1

Construction of the New Expression Vector-Family of the Invention

1. Total DNA isolation from E. coli or transducing E. coli bacteriophage DNA carrying the rrnB operon can serve as a starting material when isolating the ribosomal operon rrnB from E. coli. The rrnB operon was isolated according to the method of Kiss, A. et al. (Gene 4, (1978), 137-152) starting with transducing phage $rif^d18$ DNA, or according to the method of Boros, J. et al. (Nucl. Acids Res. 6, (1979), 1817-1830) using E. coli chromosomal DNA preparation. The first step in the construction of the expression vectors of the invention was the construction of plasmid pBB9 (MNG 00300), depicted in FIG. 1. This plasmid was created by cutting pBR322 vector plasmid (MNG 00298) (Sutcliffe, J. G., Cold Spring Harbor Symp. Quant. Biol. 43, (1978), 77-90) at the unique BamHI restriction site and ligating with the 7.5 kb BamHI-BamHI fragment of $rif^d18$ DNA. The 7.5 kb insert in the resulting recombinant plasmid carries the whole rrnB operon, some additional sequences of E. coli origin and an approx. 400 bp long sequence-element originating from the lambda phage. There are two promoters ($P_1$ and $P_2$) in the regulator, region of the rrnB operon, located 180 and 300 bp upstream of the 16S rRNA gene, respectively, (Csordás Tóth, É. et al. Nucl. Acids Res. 7, (1979), 1335-1342).

2. Recombinant plasmids comprising the rrnB operon or the promoter region thereof, owing to the strong ribosomal promoters, initiate an extremely high level of transcription which overburdens the transcription machinery of the host cell and causes instability in plasmid maintenance. To avoid this problem, we in vitro deleted all parts of the pBB9 plasmid which were not important for the further construction steps. In this step we first cleaved pBB9 DNA by HpaI restriction endonuclease and treated the resulting linear molecule with BAL31 exonuclease for different periods of time. The enzyme BAL31 gradually shortens both ends of the double stranded linear DNA molecules. The resulting DNA sample comprising linear DNA molecules of pBB9 orgin having been shortened to different extent with BAL31 exonuclease, was ligated with T polynucleptide ligase in a reaction mixture which was optimal for both blunt-end ligation and circularization, and E. coli HB101 cells were transformed with the ligation mixture. Unique transformant colonies were isolated and plasmid DNA was prepared from them. We have determined the lengths of the deletions in the selected plasmid preparations by restriction endonuclease digestion and gel-electrophoresis. We have selected plasmics with different deletive rnnB operons in which the synthesized shorter RNA molecules still had the 5' and 3' ends characteristi for mature rRNA molecules so as to obtain deletive rrnB operons still producing rRNA like molecules which are involved in the normal catabolic pathway for rRNA molecules. We named these plasmids pBB9Δ and one of them is pBB9Δ 9 (FIG. 2). On the basis of DNA sequence analysis, the deletive rrnB operon in this plasmid comprises the first 269 bp of the mature 16S rRNA molecule and the whole 5S rRNA gene at the end of the operon. The nucleotide sequence of the surrounding of the two endpoints of the deletion which are located in the first part of the 16S rRNA gene and close to the end of the 23S rRNA gene, respectively, are shown in FIG. 3.

The next step was to create further deletions in the plasmid to have the deletive rrnB operon in a plasmid as small as possible. We have linearized the plasmid pBB9Δ9 by cleaving it at the unique SalI restriction endonuclease cleavage site coming from the pBR322 vector. (There are two SalI cleavage sites in the rrMB operon but they were deleted at the previous step). We have digested the resulting linear DNA molecule with BAL31 exonuclease to get an approx. 1600 bp long shortening, for the distance between the unique SalI site and the end of the deletive rrnB operon is about 800 bp in the plasmid pBB9Δ9. We wanted to lengthen the resulting deletion in the direction opposite to the rrnB operon and to delete more nonessential parts of the vector DNA, so we also digested the shortened linear DNA molecules with PvuII restriction endonuclease before circularization. This enzyme cuts DNA resulting in blunt ends so the two ends of the linear DNA molecules—one of which was generated by PvuII and the other by BAL31 digestion—could be joined together without further modification. DNA ligation, transformation and colony selection by physical mapping were as previously mentioned. We have chosen plasmid pBB9b28 (FIG. 4) for the further construction work, in which the deletion created by SalI-BAL31-PvuII digestion was 2174 bp long. One endpoint of this deletion is located 510 bp downstream of the end of the mature 5S RNA sequence and the other endpoint is the PvuII cleavage site of the pBR322 vector, that is basepain 2067 according to the numbering of pBR322. The nucleotid sequence of the surrounding of the two deletion end points is shown in FIG. 3.

We have also created a third deletion to delete the region upstream of the promoter region of the rrnB operon. We have digested the plasmid pBB9b28 with EcoRI and FspII restriction endonucleases both of which have one recognition site upstream of the 16S rRNA gene of the rrnB operon and isolated the vector and the fragment comprising the bigger part of the deletive rrnB operon. We have filled the sticky ends of the isolated EcoRI-FspII fragments in with the Klenow fragment of DNA polimerase I and circularized it by ligating with T4 polynucleotide ligase. When joining the properly filled-in ends together both the recognition sequences of the EcoRI and FspII restriction endonucleases are reconstructed:

```
GAATTCGA
CTTAAGCTT
``` thus the resulting plasmid (p408-5, MNG00301) can be linearized with both enzymes (FIG. 5).

In the next step we have linearized plasmid p408-5 with cleaving by FspII enzyme the recognition site of which is located 100 bp upstream of the Pribnow box of promoter $P_1$ and we created a series of deletions extending to promoter $P_2$ applying limited BAL31 digestion (FIG. 5). After ligation and transformation, we have determined the endpoints of the deletions in the isolated plasmid DNA by restriction mapping with BspRI, MspI and HhaI restriction endonucleases and by DNA sequence analysis. In plasmid p419-10 the 197 bp long deletion eliminated promoter $P_1$, and ended at 100 bp upstream of promoter $P_2$. The deletion has also eliminated a 110 bp long sequence from the vector DNA, upstream of the ampicillin resistance gene. The nucleotide sequence of the surrounding of the deletion endpoints is shown in FIG. 3.

3. In the next step. We have joined this shortened rrnB operon with the beginning of the lac operon. We have isolated it on the 412 bp long HindIII-EccRI fragment from pLBU3 plasmid DNA (Gentz, R., Langer, A., Chang, A. C. Y., Cohen, S. N. and Bujard, H., Cloning and analysis of strong promoters is made possible by the downstream placement of a RNA termination signal. Proc. Natl. Acad. Sci. USA 78, (1981) 4936–40.) The isolated fragment comprises the following parts in the direction from EcoRI to HindIII: 160 bp DNA of unknown origin and function, joining to the part coming from the lac operon, 4 bp upstream of the Pribnow-box of the lac promoter. This latter part-originating from the lac operon-comprises a part of the lac promoter ($-10$ region), the whole operator, the initiation site of transcription, the ribosome binding-site near the 5' end of the mRNA, the ATG translation start codon and the coding region for the first 70 amino acids of β-galactosidase. This N-terminal polypeptide (named α-peptide) has no β-galactosidase activity but it can reconstitute a part of the activity when interacting with some special type of defective β-galactosidase molecules (α-acceptor mutants) which are also inactive themselves.

Plasmid p419-10 was cleaved by StuI restriction endonuclease between promoter $P_2$ and terminator $T_1$ and synthetic EcoRI linker was joined to the blunt ends of the resulting linear DNA molecules. The linker-plasmid ligation mixture was digested with EcoRI restriction endonuclease and ligated again in conditions optimal for plasmid circularization. Plasmid p808-2 isolated after transformation which differs from the plasmid p419-10 only in lacking of the StuI restriction endonuclease cleavage site which is substituted for EcoRI cleavage site by inserting the linker (FIG. 6). The isolated HindIII-EcoRI fragment of pLBU3 was ligated to the HindIII-EcoRI digested p808-2 plasmid DNA and E. coli cells were transformed with the ligation mixture. Transformant colonies were grown on solid medium containing indicator stain and after 24–36 hours, light-blue colonies were observed, the color indicated the low level α-peptide expression. Plasmid DNA was isolated from these colonies and it was proved by physical mapping that they carried plasmid p827-10 (MNG 00307)

which was created by the proper joining of the said two fragments (FIG. 6).

4. In the next step, deletions were created between promoter $P_2$ of the rrnB operon and the translation startpoint, so as to improve the efficiency of the translation. Plasmid p827-10 was linearized by EcoRI digestion and sequences of different length—up to 400 bp—were eliminated by BAL31 exonuclease digestion and the resulting shortened DNA molecules were recircularized by DNA ligase. Transformants showing intensive blue color (intensive synthezis of α-peptide) on the indicator plates were isolated.

In one of the resulting plasmids (PER-VI/23) the sequence of rrnB origin ends 2 bp downstream of the $-10$ region of promoter $P_2$ and the transcription and translation regulatory regions of lac origin (lac operator, ribosome binding-site, translation startpoint) are joined to promoter $P_2$ with the same spacing as it was to the lac promoter in the lac operon. This construction provides optimal conditions for translation and for the regulation of translation just as it was in the lac operon. This plasmid does not comprise the approx. 25 bp long G-C rich sequence-element downstream of the $-10$ region of promoter $P_2$ which inhibits promoter activity to different extent depending on the physiological conditions of the cell. The role of this sequence-element in regulating promoter activity was recognized in this laboratory (Lukácsovich, T. et al. J. Bact. 169, (1987) 272–277).

The transcription initiation sites of such a constructed promoter (named: 6/23, later on) is situated in the sequence of lac origin and is probably the same as that of the lac operon (GGAATT). This promoter construction carried by the plasmid pER-VI/23 provides at least an order of magnitude higher α-peptide gene expression than other similar constructions, where the different parts of rrnB and lac origin were joined together at other sites. The level of α-peptide gene expression is easy to measure by spectrophotometrical methods with the help of the so called α-complementation reaction (Miller: Experiments in molecular genetics, Cold Spring Harbor, 1972). A further advantage of the promoter construction 6/23 is the unique NsiI restriction endonuclease cleavage site created at the joining site of the two parts of different origin which makes further alterations much easier. The most useful one of such alterations is to delete the inner four nucleotide of the NsiI cleavage site (A TGCA T); which can be done e.g. by $T_4$ DNA-polymerase treatment after the cleavage by NsiI endonuclease, $T_4$ DNA-polymerase digests the four excised nucleotides of the NsiI cleaved sticky end. When ligating the so treated plasmid molecule by $T_4$ DNA-ligase a promoter construction is obtained in which the $-10$ region of promoter $P_2$ remains intact while the transcription initiation site is shifted a few basepairs downstream. Because of not perfectly understood reasons, this alteration further increases the transcription efficiency without changing translation efficiency or regulatory features. These plasmid and promoter constructions will be named: pER-VI/23[−Nsi] and 6/23[-Nsi], respectively. FIG. 7 shows the sequences of the promoters 6/23 and 6/23[-Nsi].

5. Plasmids pER-VI/23[-Nsi] and pER-VI/23 meet most of the requirements for expression vectors. A significant disadvantageous feature of them is, however, the limited possibility to build in foreign genes. This is only made possible by the two unique restriction endonuclease cleavage sites: PvuII and HindIII situated in the coding region of the α-peptide and immediately after this region, respectively. The aim of the further alterations was to create a family of vectors making possible to build foreign genes in with the help of many commonly used restriction endonucleases in all the three reading frames. When constructing this vector-family, a further requirement was to make possible the expression of the foreign gene both as an individual protein and as a fusion-protein, where it is fused to a stable protein of E. coli. (This latter solution is needed when the half-life of the foreign protein to be expressed is very short in the bacterial cell, e.g. human proinsuline. In such cases, the N-terminal part of the fusion protein, which is of E. coli origin, can protect the unstable foreign protein from degradation).

Construction of a vector-family meeting the above requirements—named: vector-family pER-VI/23—will be described later on. After the construction of these pER-VI/23 type plasmids, pER-VI/23[-Nsi] type plasmids were created according to the above described method. An enhancement in the level of gene expression was experienced in all cases.

As a first step, a 109 basepair long HindIII—HindIII polylinker of πVX miniplasmid origin (T. Maniatis et al., Molecular cloning, A laboratory manual; Cold Spring Harbor, (1982), p. 353) was cloned in both orientations to the unique HindIII cleavage site of the plasmid pER-VI/23. This polylinder comprised ClaI, EcoRI, BamHI, PstI, BglII and XbaI restriction endonuclease cleavage sites besides the two HindIII cleavage sites (see FIG. 8). The resulting plasmids were named: pER-VI/23 PLH4 and pER-VI/23 PLH5, containing the polylinker in the orientation showed in FIG. 8 and in the opposite orientation, respectively. In these plasmid constructions and derivatives thereof there is at least one unique restriction endonuclease cleavage site in all the three reading-frames situated in the polylinker region which makes possible to build in any foreign gene to be expressed together with the α-peptide as a fusion protein. It is known from the art that different foreign genes must be fused to β-galactosidase parts of different length to get maximum protection. We, therefore, constructed two more members of the said vector-family. The 733 bp long PvuII-ClaI fragment of the lacZ gene (the gene coding for β-galactosidase in E. coli) was cloned into the PvuII-ClaI sites of plasmid pER-VI/23 PLH4. This fragment codes for further 244 amino acids of β-galactosidase. The resulting plasmid was named: pmed/23.

The 1621 bp long PvuII-EcoRV fragment of the lacZ gene was blunt-end ligated to the 150 bp long PvuII-EcoRI fragment of the gene coding for chloramphenicol-acetyl-transferase (CAT; originating from plasmid pBR329, Gene 17, (1932) 79–89), joining the EcoRV and PvuII blunt-ends together. The resulting 1771 bp long PvuII-EcoRI fragment—which is one long open reading-frame—was cloned into the PvuII-EcoRI sites of plasmid pER-VI/23 PLH4. The resulting plasmid was named: pl-alpha Int/23. The high copy-number versions of plasmids pER-VI/23 PLH4, pER-VI/23 PLH5 and pl-alpha Int/23 have also been constructed (see Hungarian Patent Application published under No. T/35280).

With the help of the said members of the vector-family, any foreign protein can be expressed as a part of a fusion protein, the first 70 (pER-VI/23 PLH4, pER VI-23 PLH5), the first 280 (pmed/23) or the first 390 (pl-alpha Int/23) aminoacids of which are of E. coli origin (β-galactosidase, CAT). FIG. 9 shows the schematic representation of the said plasmids.

The above vector-constructions also make possible to express intact foreign genes in a non-fusion form. This will happen if we build the foreign gene in so as the translation starting on the coding region of *E. coli* origin(lacZ or lacZ+CAT) stops immediately before the start codon of the foreign gene to be expressed, and/or the foreign gene has a strong *E. coli* ribosome binding-site. In this case, the construction works similarly to a bacterial operon comprising two genes. However, in a system comprising two genes, optimization of gene expression is often hard to achieve (the result is uncertain), that is why we developed new members of the above vector-family which are of general use in the expression of intact genes. To reach this goal, we had to delete the region coding for the α-peptide from the plasmid pER-VI/23 PLH4 so that the lac regulatory sequences remain, and we had to build a suitable restriction endonuclease cleavage site into the plasmid with optimal spacing to the lac regulatory sequences. The first step of this construction work was to clone the small NsiI-AluI fragment of plasmid pER-VI/23 PLH4 (see FIG. 7) into the unique NsiI-PvuII sites of the same plasmid. As it can be seen in FIG. 7, the said AluI site is immediately upstream of the translation start codon and it is also clear that, at the same time, the left half of this AluI cleavage site is a half PvuII cleavage site. Therefore, if the joining of the said two fragments is correct, the unique PvuII cleavage site of plasmid pER-VI/23 PLH4 will be regenerated. The resulting plasmid was named: pER-VI/23 [-ATG], for this construction is suitable for expressing foreign genes having their own ATG translation start codon.

These types of foreign genes can be built into the newly created PvuII cleavage site after making them blunt-ended. The effective expression of the foreign gene is possible if it has not more than 8 basepairs: (preferably 4 bp) upstream of the ATG codon. In this case the spacing between the translation start codon of the foreign gene and the ribosome binding-site of lac origin is optimum or close to that.

To make easier the expression of synthetic genes, plasmid pER-VI/23[-ATG] was further modified. A synthetic ClaI linker (comprising a ClaI cleavage site) was built into the said unique PvuII restriction cleavage site. The fragment between the newly created ClaI site and the ClaI site in the polylinker region of the plasmid was deleted. This was done by recirculation of the bigger fragment after cleaving the plasmid by ClaI restriction endonuclease. The resulting plasmid was named pER-VI/23[+ATG]. This plasmid is extremely suitable for the expression of foreign genes having no ATG translation start codon (for synthetic genes, mainly). Any foreign gene like this can be built into the ClaI site of this plasmid after joining ClaI linkers to its ends. In this case—when the orientation of the insert is correct—the translation of the foreign gene will start at the ATG sequence of the ClaI linker. The distance between this ATG codon and the ribosome binding-site of lac origin is 8 bp which is optimum in *E. coli*. This vector is of course also very suitable for the expression of foreign genes having their own ribosome binding-site. Cloning of such genes is made easy by the restriction endonuclease cleavage sites situated in the polylinker region of the plasmid (ClaI, EcoRI, BamHI, PstI, BglII, XbaI, HindIII). FIG. 10 shows the schematic representation of plasmids pER-VI/23 [-ATG] and pER-VI/23 [+ATG]

As it has been said before, deleting the inner 4 basepairs of the unique NsiI cleavage site from each of the above plasmids we constructed the vector-family pER-VI/23[-Nsi], according to the above mentioned procedure.

In the following part of this application, we give examples of the utilization of some members of the vector family pER-VI/23[−Nsi].

EXAMPLE 2

Proving the Effective Gene-Expression Provided by the Expression Vectos of the Invention We have made a direct comparison to prove that expression vector-family of the invention really provides more effective gene expression than those known from the art.

A plasmid construction was made using the expression vector pKK223-3 comprising the above mentioned "ideal" (consensus) promoter (tac promoter) as a starting material (by J. Brosins; Pharmacia, Molecular Biologicals No. 27-4935-01), which has a perfectly identical nucleotide sequence to that of plasmid pER-VI/23 in the whole α-peptide coding region and in both the 3' and 5' nontranslated regions. These two plasmids are of the same replication type (Col 1) so if they provide different amounts of α-peptide or of its mRNA, it is probably only caused by the difference between the two promoters they carry.

This comparison is not affected by the mRNA halflife or by translation efficiency etc. because the two mRNA-s produced by the different plasmids are identical.

The mRNA produced by plasmid pER-VI/23[-Nsi] is four basepairs shorter than the mRNA-s produced by the above two plasmids, in other respects it is perfectly identical. Comparing the three plasmids by measuring both the amounts of the produced mRNA and α-peptide we have found the same order: pER-VI/23[-Nsi]; pER-VI/23; pKK223-3 derivative, where each vector provides 1.5-2.0 times higher expression than the next one.

In the following examples we have also examined the expression vectors of the invention as models.

EXAMPLE 3

Producing Protein in *E. coli* with the Help of The New Vector-Family Without Building Foreign Gene Without building in a foreign gene, the level of the expression of the α-peptide (the N-terminal part of β-galactoridase in plasmids p med VI/23 [-Nsi] and pL-alpha Int/23 [-Nsi] can be determined not only by measuring its enzyme activity but the amount of the protein produced can also be measured by SDS-polyacrylamide gel-electrophoresis. In suitable lac I$^q$ host cells, α-peptide production can not be seen without induction. When a bacterium culture growing in YTB medium at 37° C., being in logarithmic phase, is induced by adding 0.1-5 mM IPTG, gene expression starts from promoter 6/23 [-Nsi] and the expressed protein accumulates in the bacterial cells up to 20-60% of the total cellular protein.

EXAMPLE 4

Producing Protein in *E. coli* Using the New Vector-Family after Building in a Foreign Gene To demonstrate that the new vector-family of the invention is of general use and is suitable for the expression of both small and large proteins (expression of large proteins is generally problematic in *E. coli*), we carried out the following experiment:

1. The ClaI-PstI fragment of a cloned lac operon of *E. coli* was built into the ClaI-PstI site of plasmid pL-alpha Int/23 [-Nsi] (applying partial PstI digestion we cleaved only one of the PstI sites). The whole coding sequence of the lacZ gene was built in, this way. The product of the lacZ gene, the enzyme β-galactosidase, is one of the largest proteins of *E. coli* (Mw: 135000). In a suitable host strain it is possible to overproduce this enzyme to a significant extent (up to 15-30% of total cellular protein), after IPTG induction, in an enzymatically active form.

2. Expression vectors of the invention can also function as a bacterial operon comprising two genes. We examined this functioning using two different foreign genes of bacterial origin. The first such gene was the above mentioned chloramphenicol-acetyl-transferase gene which was isolated from plasmid pBR329.

TaqI fragment isolated from pBR329 was cloned into the ClaI site of plasmid pER-VI/23 [-Nsi] PLH4. In this construction CAT gene is expressed from promoter 6/23 [-Nsi] using its own ribosome binding-site. The translation process goes on one long mRNA molecule which is common for the α-peptide and CAT genes. After polyacrylamide gel-electrophoresis of the total cellular protein of the induced cells, the two strongest protein bands correspond to the α-peptide and the CAT-protein. This plasmid construction was also modified to a plasmid expressing fusion-protein. The first step of this modification was to delete the downstream HindIII cleavage site of the polylinker region. This was done by BAL31 exonuclease digestion after XbaI cleavage and by recircularization by T4 ligase afterwards. A further deletion was created thereafter by cleaving the plasmid at the remaining unique HindIII site, BAL31 digestion and recircularization. The resulting plasmid expresses CAT gene as an α-peptide fusion-protein, and this protein is a bifunctional enzyme (α-complementation of β-galactoridase and acetyl transfer on chloramphenicol). In suitable conditions, the accumulation of this fusion protein will reach 80% of the total cellular protein. (Both above plasmids provide resistance to chloramphenicol for the host cells to an extent depending on the level of induction).

3. The other overproduced foreign gene of bacterial origin was the gene coding for the modification methylase gene in Bacillus sphaericus (BspRI modification methylase). In spite of the fact that the product of this gene strongly affects the metabolism of the E. coli cell (being a DNA binding and methylating enzyme), the accumulation of this protein can reach 2-4% of the total cellular protein using the expression vectors of the invention.

In the experiments described in the examples we used the following materials and methods.

CHEMICALS AND OTHER PREPARATIONS

Laboratory chemicals of general use were of pro anal. quality bought from the firms: REANAL, SIGMA and MERCK.

γ-$^{32}$P-ATP and α-$^{32}$P-dATP preparations were from the Hungarian Institute of Isotopes (IZINTA, Budapest) with specific activities; 100-150 TBq/mM.

Restriction endonucleases BamHI, HpaI, SalI, PvuII, EcoRI, BspI, HindIII, PstI, BglII, XbaI, FspII were isolated in the Biological Research Center of the Hungarian Academy of Sciences according to published procedures (Methods in Enzymology, Ed; L. Grossman. V. Meldave. Vol. 65, pp. 89-180). Restriction endonucleases ClaI, StuI, HhaI were from New England Biolabs.

BAL31 exonuclease and Klenow-enzyme (*E. coli* DNA-polymerase I Large Fragment) were from New England Biolabs; Bacterial alkaline phosphatase (BAP) was from Worthington; pancrease RN-ase and lysosyme were from REANAL.

T$_4$ induced polynucleotide ligase was prepared according to the method of Murray et al. (Murray, N. E., Bruce, S. A. and Murray, K: Molecular cloning of the DNA ligase gene from bacteriophage T$_4$, J. Mol. Biol. 132 (1979), 493-505).

STRAINS AND PLASMIDS

*Escherichia coli* HB101 (pro, leu, thi, lac, str$^R$, r, m, endoI, recA: Boyer, H. W., Roulland-Dussoix, D: A complementation analysis of the restriction and modification of DNA in E. coli, J. Mol. Biol. 41 (1969), 459-472; MNG 00291).

Escherichia coli ED8800 (supE, supF, hsdS, met, lacZM15, recA56: Murray, N. E., Brammar, W. J. and Murray, K: Lamboid phages that simplify the recovery of in vitro recombinants, Mol. Gen. Genet. 150 (1977), 53-61; MNG 00291).

rif$^d$ 18 (Kirschbaum, J. B. and Konrad, E. B. Isolation of a specialized lambda transducing bacteriophage carrying the beta subunit gene for Escherichia coli ribonucleic acid polymerase, J. Bacteriol 116 (1973) 517-526).

pBR322(Bolivar, F., Rodrigues, R. L. Green, P. J., Betlach, M., Heyneker, H. L., Boyer, H. W., Crosa, J. and Falkow, S: Construction and characterization of new cloning vehicles. Gene 2, (1977), 95-113; MNG 00298).

plBU3 (Gentz, R., Langer, A., Chang, A. C. Y., Cohen, S. N. and Bujard, H: Cloning and analysis of strong promoters is made possible by the downstream placement of a RNA termination signal. Proc. Natl. Acad. Sci. USA 78, (1981) 4936-401).

pHC314 (Boros, I., Pósfai, Gy. and Venetianer, P: A method for constructing high copy-number plasmid vectors, 1984, Hungarian Patent Application No. 3212/83; MNG 00980).

*E. coli* K12 JM107 (Yanisch-Perron, C. et al: Improved M13 phage cloning vectors and host strains: nucleotide sequences of the M13mp18 and pUC19 vectors, Gene 33; (1985), 103-119).

*E. coli* strains were grown in rich liquid media containing 10 g Bacto-tryptone, 5 g Bacto Yeast extract and 5 g NaCl per liter. Solid medium was made by adding 15 g Bacto-agar per liter to the above liquid medium. Indicator plates suitable for estimating α-peptide expression comprised:

| | |
|---|---|
| casaminoacids | 20 g |
| Na$_2$HPO$_4$ | 6 g |
| KH$_2$PO$_4$ | 3 g |
| NaCl | 0.5 g |
| NH$_4$Cl | 1 g |
| Bacto-agar | 15 g |
| X-gal (in dimethyl-formamide solution) | 20 mg |
| MgCl$_2$ | 2 mM |
| CaCl$_2$ | 0.1 mM |
| H$_2$O | 1 liter |

Strains carrying plasmids comprising the gene coding for β-lactamase were grown in a media containing 100 μg/ml ampicillin.

Isolation of plasmid DNA was made by growing the bacterium strain carrying the plasmid in a medium containing 100 μg/ml ampicillin and adding 170 μg/ml chloramphenicol to the medium at $OD_{600\ nm}=0.7-0.8$ to tamplify plasmid DNA. Laboratory scale plasmid isolation was made according to the method of Clewell and Helinski (Clewell, D. B. and Helinski, D. R: Supercoiled circular DNA-protein complex in *Escherichia coli*: purification and induced conversion to an open circular DNA form. Proc. Natl. Acad. Sci. USA 62 (1969), 1159-1166.) The resulting clear lysate was further purified by Sephacryl S1000 (Pharmacia) chromatography or by ultracentrifugation in cesium chloride/ethidium bromide gradient. Analytical scale plasmid isolation (from 1.0-1.5 ml bacterium culture) was made by the potassium acetate method of Birnboin and Doly modified by Ish-Horovitz (Maniatis, T., Fritsch, E. F. and Sambrook, J., Molecular cloning, Cold Spring Harbor Lab., New York, 1982).

Cleavage of DNA samples by restriction endonucleases was carried out according to the conditions suggested by New England Biolabs.

Sticky DNA ends were made blunt-ended as follows: DNA was precipitated by ethanol after the restriction cleavage, and was redissolved up to 10-20 μl in a buffer containing: 50 mM Tris-HCl (pH=7.4), 7 mM $MgCl_2$, 1 mM dithiothreitol, 0.1 mM dATP, 0.1 mM dCTP, 0.1 mM dGTP and 0.1 mM TTP (concentration of DNA was 200-250 μg/ml). This reaction mixture was incubated for 15 minutes at 37° C. after adding 1-2 units of DNA polymerase I Klenow fragment.

Sticky DNA ends were ligated in a reaction mixture (30-40 μl) containing 0.5-1.0 μg DNA, 66 mM Tris-HCl (pH=7.6), 5 mM $MgCl_2$, 5 mM dithiothreitol, 1 mM ATP and 1 unit of $T_4$ induced polynucleotide ligase. The ligation mixture was incubated at 14° C. for 2-3 hours (Mariatis, T., Fritsch, E. F. and Sambrook, J: Molecular cloning, Cold Spring Harbor Lab., New York, 1982). Blunt-ended DNA fragments were ligated in a mixture containing 30-40 μg/ml DNA, 25 mM Tris-HCl (pH=7.4), 5 mM $MgCl_2$ 5 mM dithiothreitol, 0.25 mM spermidin, 1 mM ATP, 10 μg/ml BSA (Sigma, Type V). After adding 4-6 units of $T_4$ induced polynucleotide ligase, the reaction mixture was incubated at 14° C. for 8-12 hours.

Agarose (Sigma, Type I) gel-electrophoresis of DNA samples was done in horizontal electrophoresis tanks according to the method of Helling et al. (1974) applying 0.8-2.0% agarose slab gels. Polyacrylamide gel-electrophoresis of DNA samples was done in vertical apparatuses, using 4 and 8%, 1 mm thick slab gels, according to the method of Maniatis et al. (Maniatis, I., Jeffrey, A. and van de Sande, H: Chain length determination of small double and single-stranded DNA molecules by polyacrylamide gel electrophoresis. Biochemistry 14, (1975) 3787-3794).

Isolation of DNA fragments from agarose and polyacrylamide gels was done using DEAE-paper, according to the method of Winberg, G. and Hammarskjöld, M. (Isolation of DNA from agarose gels using DEAE-paper. Application to restriction site mapping of adenovirus type 16 DNA, Nucl. Acids Res. 8, (1980) 253).

BAL31 exonuclease digestion of DNA fragments was done in a reaction mixture containing 100 /μg/ml DNA, 600 mM NaCl, 12 mM $CaCl_2$, 20 mM Tris-HCl (pH=8.0), 1.0 mM EDTA, at 30° C.

Depending on the required extent of shortening, 0.4-1.2 units of the enzyme was added to the mixture containing 1.0 μg DNA. A test reaction was carried out in every cases on each given DNA fragment with the given enzyme-preparatum to determine the actual rate of shortening, by gel-electrophoresis of the samples after different incubation times. The enzymatic reaction was stopped by extracting the reaction mixture with phenol and after ethanol-purification DNA ends were made blunt-ended by Klenow polymerase under conditions proper for labelling 3' ends (Maniatis, T., Fritsch, E. F. and Sanbrook, J: Molecular cloning, Cold Spring Harbor Lab., New York, 1982).

Competent E. coli cells were made from the strains HB101, C600, IM107 and ED8800, according to the $CaCl_2$ method of Mandel and Higa (Maniatis, T., Fritsch, E. F. and Sambrook, J: Molecular cloning, Cold Spring Harbor Lab., New York, 1982).

Dephosphorilation of the 5' ends of the DNA fragments, end-labelling with polynucleotide kinase using $\gamma$-$^{32}$P-ATP and nucleotide sequence analysis was made according to the method of Maxam, A. and Gilbert, W. (Sequencing end-labelled DNA with basespecific chemical cleavages. Meth. Enzymol. 65, (1980) 499-560).

Other methods used in our vector construction work were according to the protocols presented in the laboratory manual of Maniatis, T., Fritsch, E. F. and Sambrook, J. (Molecular cloning, Cold Spring Harbor Lab., New York, 1982).

Structure of Plasmid pBB9

The part of pBR322 origin is drawn in double line, and the part of $rif^d$ 18 origin is signed by thick line. The most important genes and regulatory regions are indicated within the circle. Restriction endonuclease cleavage sites are indicated by arrows. Abbreviations:

$amp^r$: gene for β-lactamase providing resistance to ampicillin;

$tet^r$: gene for resistance to tetracyline (because of the DNA fragment inserted into the BamHI site, the tetracycline resistance gene was inactivated);

λ: the part of lambda origin in the fragment coming from the transducing phage $rif^d18$; 5S; 16S; 23S: genes for the different mature RNA molecules of operon rrnB; $P_1$; $P_2$: promoters of operon rrnB; $T_1$; $T_2$: terminators of operon rrnB; P: PstI; E: EcoRI; H:HindIII; B:BamHI; S:SalI; Hp:HpaI; Pv:PvuII; F:FspII.

FIG. 2

Structure of Plasmid pBB9Δ9

Shaded area means the part which was deleted from plasmid pBB9 by BAL 31 exonuclease digestion. Abbreviations are as in FIG. 1.

FIG. 3

Nucleotide Sequence of the Surrounding of the Joining Point of the Two Parts of Different Origin in Plasmid pER-VI/23.

FIG. 4

Structure of Plasmid pBB9-b28

Figure 1:
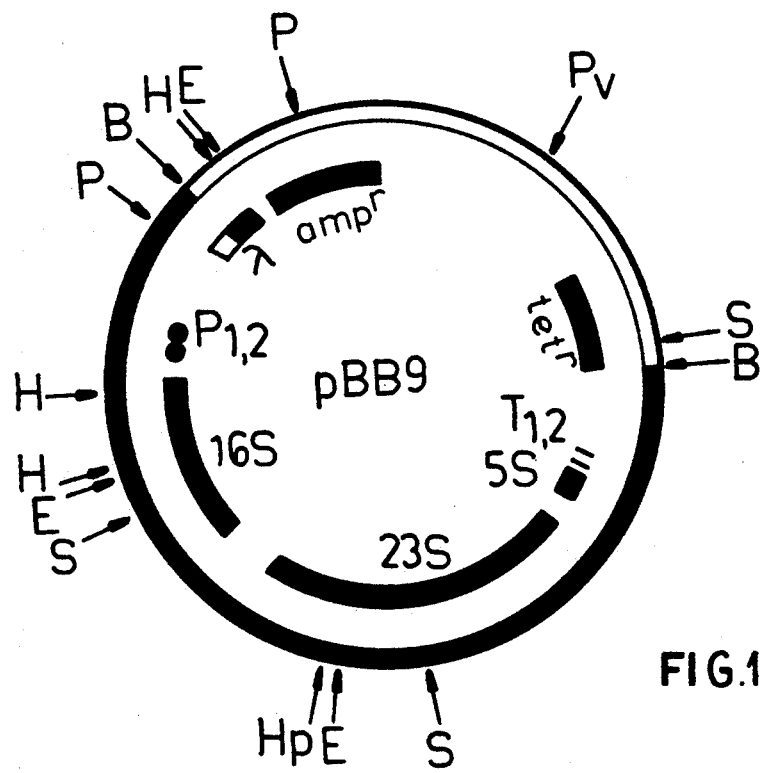
FIG. 1
Figure 2:
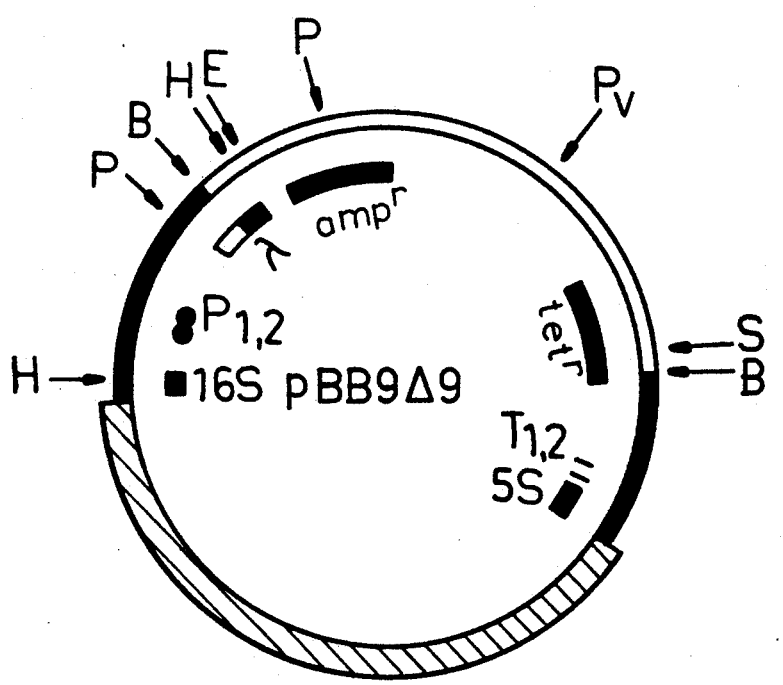
Figure 4:
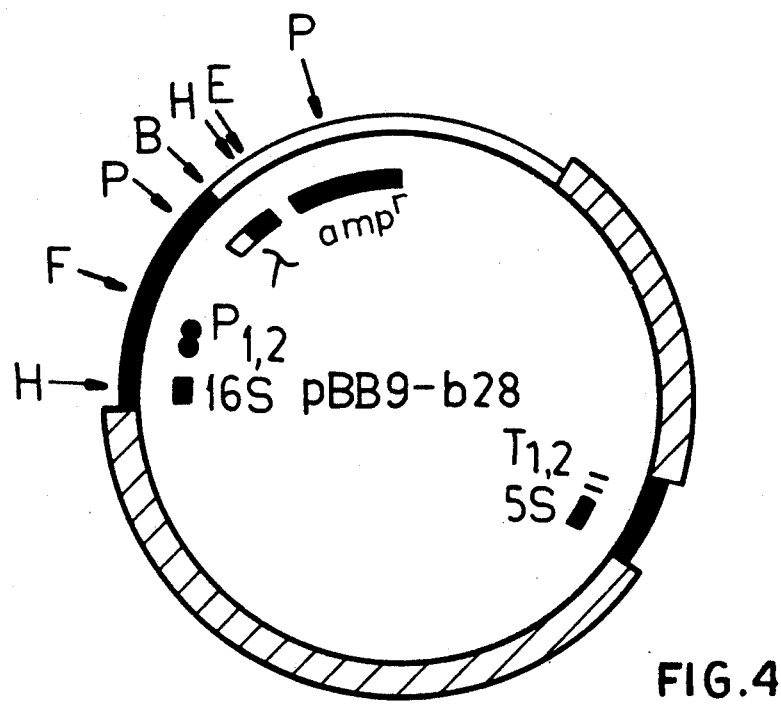
Figure 5:
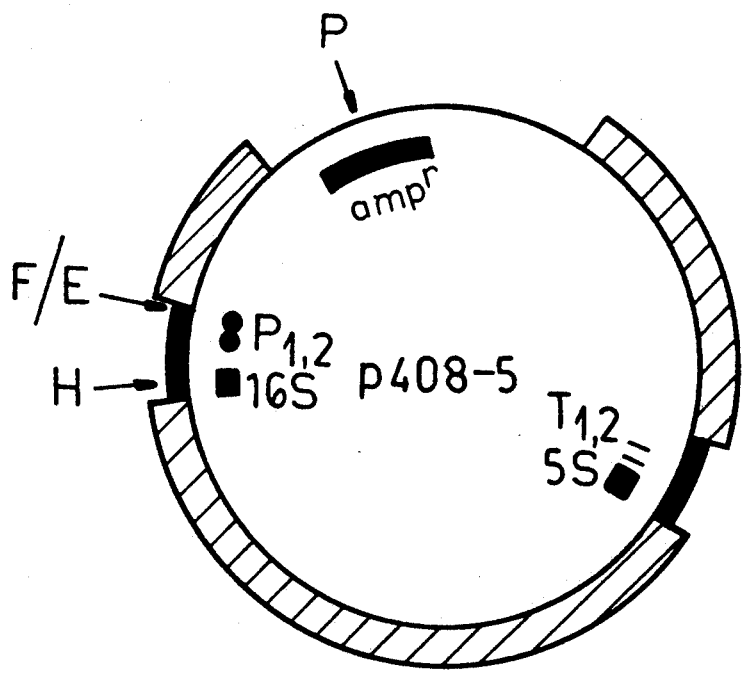
Figure 6:
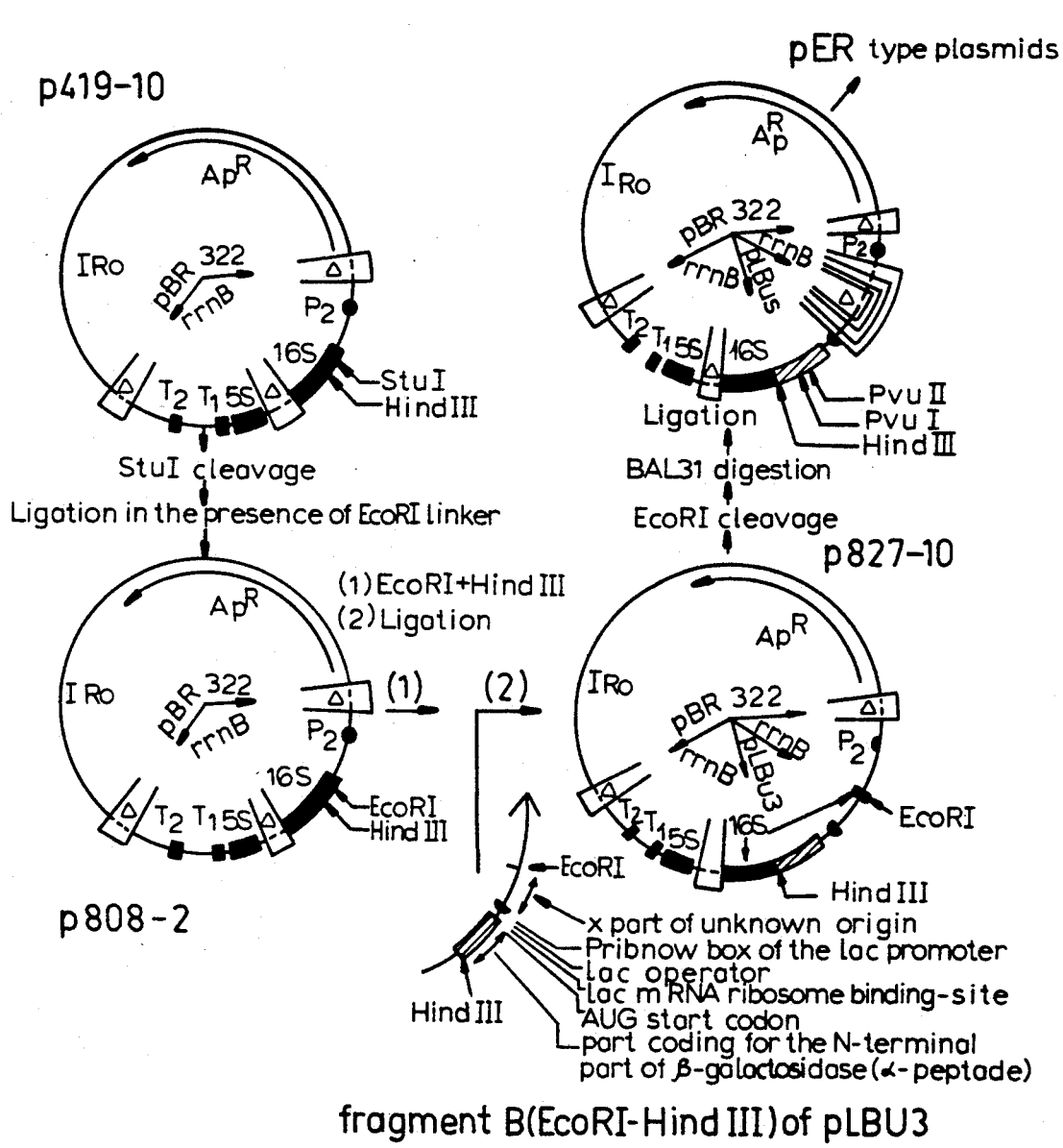

Designations and abbreviations are as in FIGS. 1 and 2. Shaded areas mean parts deleted from plasmid pBB9.

FIG. 5

Structure of Plasmid p408-5

Designations are as above.

FIG. 6

Building Together Parts of Operons rrnB and lac to get pER Type Plasmids

Construction of pER type plasmids from plasmid p419-10 and fragment "B" (EcoRI-HindIII) of plasmid plBU3 is depicted in detail.

Abbreviations: $Ap^R$: gene for resistance to ampicillin; Ro: replication origin; $T_1$ and $T_2$: terminators of operon rrnB; $P_2$: one of the promoters of operon rrnB; 16S and 5S: remaining parts of operon rrnB. "Gates" mean deletions. Upper right panel represents plasmid-family pER, members of which only differ from each other in the length of the BAL31 deletion. (Multiple "gates" around a Δ symbol mean deletions of different length.)

FIG. 7

Nucleotide Sequence of the Promoters in Plasmids pER VI/23 and pER VI/23 [-Nsi]

Joining parts originating from rrnB and lac operon, respectively, a) in plasmid pER VI/23 and b) in plasmid pER U/23[-Nsi].

| Designations: | | |
|---|---|---|
| ... : | AT-rich pre-promoter region upstream of rrnB $P_2$ | |
| : | −35 region of promoter 6/23 which is of rrnB origIn | |
| : | −10 region of promoter 6/23 which is of rrnB origin | |
| xx: | transcription initiation site | |
| : | ribosome binding-site of lac origin | |

The part of the sequence written in block letters comes from operon rrnB and the other part written in italics is of lac origin. The operator gene of the lac operon and the first few amino-acids of α-peptide are signed under the sequence.

FIG. 8

Nucleotide Sequence of the HindIII—HindIII polylinker of π VX Origin in the Orientation as it is in the PLH4 Type Plasmids.

Figures 9, 10:
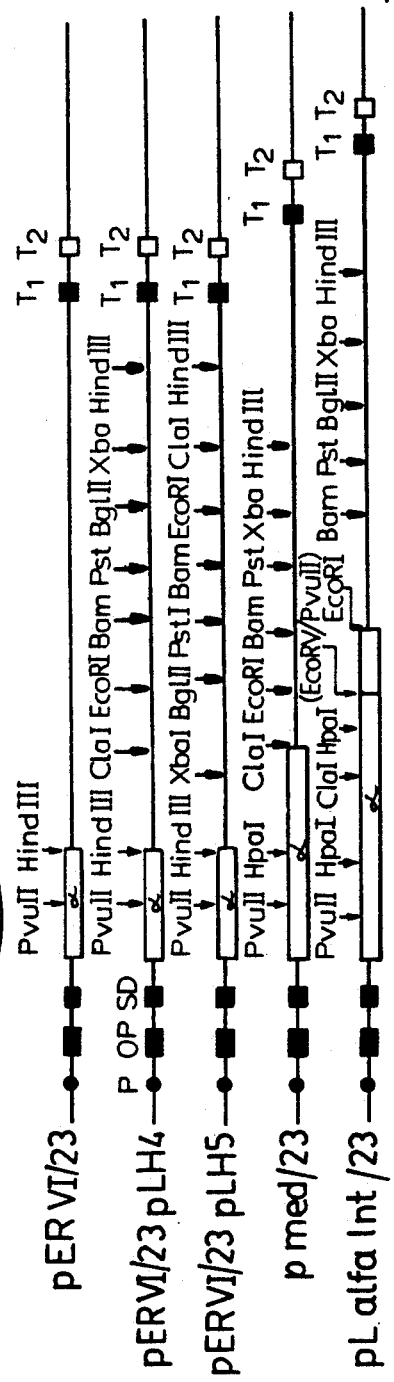

FIGS. 9 and 10

Schematic representation of the new expression vector-family

The gene for resistance to ampicillin ($Ap^R$), the replication origin (ORI), promoter 6/23/[-Nsi] (p), the ribosome binding-site (SO) and the two terminatory regions ($T_1$, $T_2$) are signed on the circle representing the plasmid molecules. The part signed by wavy line is characteristic for the individual members of the plasmid-family. The detailed representations of this part of the molecule include some more abbreviations as follows. α: sequences coding for different parts of β-galactosidase; CAT: sequences coding for chloramphenicol-acetyl-transferase. Restriction endonuclease cleavage sites suitable for cloning are also indicated (PvuII, HindIII, ClaI, EcoRI, BamHI, PstI, BglII, XbaI, HpaI). (EcoRV/PvuII) means two restriction sites which were built together and can not be recut with any one of the enzymes.

STRAINS DEPOSITED

| Sign of the strain/plasmid | Deposition No. | Date of deposition |
|---|---|---|
| pBB9 | MNG 00300 | 31.10.1984. |
| pBR322 | MNG 00298 | 12.11.1984. |
| p408-5 | MNG 00301 | 31.10.1984. |
| p827-10 | MNG 00307 | 31.10.1984. |
| E. coli HB101 | MNG 00290 | 25.07.1984. |
| pER VI/23 ENs: | NCAIM 8/P 001016 | 18.06.1987. |
| pER VI/23 pLH4 | NCAIM B/P 001014 | 18.06.1987. |
| pER VI/23 pLH5 | NCAIM B/P 001015 | 18.06.1987. |

We claim:

1. A promoter constructed by joining together promoter $P_2$ of a ribosomal RNA operon rrn B of *Escherichia coli* and a regulatory sequence of the lac operon of *Escherichia coli* outside the regions −35 and −10, downstream from the region −10, said regulatory sequence having the formula:

AATTGTGAGCGGATAACAATTT-CACACAGGAAACAGCTATGACC, and said promoter having a deletion of the TGCA sequence element immediately downstream of the region −10.

2. An expression vector, carrying the promoter defined in claim 1.

3. An expression vector carrying the promoter of claim 1, further carrying the lac operator, a ribosome binding site, a translation start site, a sequence coding for a sufficient number of the first 244 N-terminal amino acids of beta-galactosidase to form a fusion protein in which said fusion protein retains the biological activity of beta-galactosidase with a protein to be expressed, one or more restriction endonuclease cleavage sites as defined in FIG. 9 or FIG. 10, transcription terminators, a gene coding for resistance to ampicillin and a replication origin functioning in *E. coli*.

4. Expression vectors as depicted in FIG. 9 and FIG. 10.

5. *E. coli* cells transformed by expression vectors according to claim 2.

6. A method for constructing the promoter of claim 1 comprising the steps of joining together promoter $P_2$ of a ribosomal RNA operon (rrn B) of Escherichia coli with the beginning part of the lac operon outside the regions −35 and −10, immediately downstream of them, so as to create a new NsiI restriction endonuclease cleavage site at the joining point of the sequences originating from the rrn B and lac operons, and deleting the inner TGCA sequence-element from the newly created NsiI cleavage site.

7. A method for constructing an expression vector according to claim 2 comprising the steps of joining together promoter $P_2$ of a ribosomal RNA operon (rrn B) of *Escherichia coli* with the beginning part of the lac operon outside the regions −35 and −10, immediately downstream of them, so as to create a new NsiI restriction endonuclease cleavage site at the joining point of the sequences originating from the rrn B and lac operons, deleting the inner TGCA sequence-element from the newly created NsiI cleavage site and inserting a gene to be expressed downstream of these newly created regulatory sequences.

8. The method of claim 7, characterized by using a rrn B operon comprising a deletion ending in the sequence coding for the mature RNA molecules, for the construction of the expression vector.

9. The method defined in claim 7, characterized by using plasmid pBR322 as vector molecule.

10. A method for overproduction of proteins in *E. coli* host cells, characterized by using an expression vector defined in claim 2.

11. A promoter of the following nucleoide sequence:

AGAGAAAGCAAAAATAAATGC<u>TTGACT</u>CTGTAGCGGGAAGGCCG<u>TATTA</u>
    region—35                                  region—10 (minus)
    part of rrnB origin                   one T nucleotide)
TGGAATTGTGAGCGGATAACAATTTCACACAGGAAACAGCTATGACC part of lac origin.

\* \* \* \* \*